US012753250B2

(12) United States Patent
Hong et al.

(10) Patent No.: US 12,753,250 B2
(45) Date of Patent: Oct. 6, 2026

(54) AMINATION METHOD FOR POLYSTYRENE-TYPE RESIN, AND METHOD FOR IMMOBILIZING ENZYME USING AMINATED RESIN

(71) Applicant: Asymchem Laboratories (Tianjin) Co., Ltd., Tianjin (CN)

(72) Inventors: Hao Hong, Morrisville, NC (US); Yi Xiao, Tianjin (CN); Na Zhang, Tianjin (CN); Han Lin, Tianjin (CN); Long Pan, Tianjin (CN); Williams Vyasa, Morrisville, NC (US); Liteng Ma, Tianjin (CN); Yuxia Cui, Tianjin (CN); Yanyan Gao, Tianjin (CN)

(73) Assignee: Asymchem Laboratories (Tianjin) Co., Ltd., Tianjin (CN)

( * ) Notice: Subject to any disclaimer, the term of this patent is extended or adjusted under 35 U.S.C. 154(b) by 500 days.

(21) Appl. No.: 18/552,808

(22) PCT Filed: May 10, 2021

(86) PCT No.: PCT/CN2021/092799
§ 371 (c)(1),
(2) Date: Sep. 27, 2023

(87) PCT Pub. No.: WO2022/205565
PCT Pub. Date: Oct. 6, 2022

(65) Prior Publication Data

US 2024/0191008 A1 Jun. 13, 2024

(30) Foreign Application Priority Data

Mar. 29, 2021 (CN) ........................ 202110329787.6

(51) Int. Cl.
*C08F 112/08* (2006.01)
*C08F 8/32* (2006.01)
*C12N 11/082* (2020.01)

(52) U.S. Cl.
CPC .............. *C08F 112/08* (2013.01); *C08F 8/32* (2013.01); *C12N 11/082* (2020.01)

(58) Field of Classification Search
None
See application file for complete search history.

(56) References Cited

U.S. PATENT DOCUMENTS 4,206,259 A * 6/1980 Rohrbach .............. C12N 11/14
502/7

FOREIGN PATENT DOCUMENTS

| | | | | |
|---|---|---|---|---|
| CN | 101776686 A | * 7/2010 | | |
| CN | 102260662 A | 11/2011 | | |
| CN | 106222157 A | 12/2016 | | |
| CN | 108956989 A | 12/2018 | | |
| CN | 112546976 A | 3/2021 | | |
| CN | 112707977 A | 4/2021 | | |
| JP | S63196278 A | 8/1988 | | |
| JP | 2003024800 A | 1/2003 | | |
| WO | 0005325 A1 | 2/2000 | | |
| WO | WO-2018187945 A1 | * 10/2018 | ............ | C08F 110/02 |

OTHER PUBLICATIONS

CN 101776686 A, 2010, machine translation (Year: 2010).*
WO 2018187945 A1 , 2018, machine translation (Year: 2018).*
Chinese Patent Office, Office Action for CN Appl No. 2021103297876, dated Apr. 6, 2021 (2 pages).
European Patent Office, Extended Search Report regarding European Application No. 21934216.9, mailed Sep. 16, 2024 (5 pages).
Japanese Patent Office, Office Action for JP Appl No. 2023-559817, dated Oct. 29, 2024 (2 pages).
Li, S.-S & Zhang, H.-J & Zhou, M. & Zhang, Z. & Wang, C.-W & Luo, G. & Liu, Q.. (2017). Progress on functionalization of polystyrene microsphere and its application. Xiandai Huagong/Modern Chemical Industry. 37. 38-41 and 43. 10.16606/j.cnki.issn0253-4320.2017.05.009 (5 pages).

(Continued)

*Primary Examiner* — Satya B Sastri
(74) *Attorney, Agent, or Firm* — MCANDREWS HELD & MALLOY, LTD

(57) ABSTRACT

Provided is an amination method for a polystyrene-type resin, and a method for immobilizing an enzyme using an aminated polystyrene-type resin. The amination method includes: in a solvent, a catalyst is used to catalyze a polystyrene-type resin and an enamine salt to perform a Friedel-Crafts alkylation reaction, to obtain an aminated polystyrene-type resin, herein the catalyst is a Lewis acid catalyst. By means of the Friedel-Crafts alkylation reaction, the enamine salt is grafted onto the polystyrene-type resin, and the polystyrene-type resin is aminated. The conditions of the Friedel-Crafts alkylation reaction are easy to control, the post-treatment process is simple, and it is only necessary to remove the catalyst and the unreacted enamine salt by washing. Therefore, the above amination method in the present application has few steps and is simple and easy to implement. Meanwhile, the amination method further avoids the use of a noble metal catalyst, thereby reducing production cost. When the obtained polystyrene resin is used as an enzyme immobilization carrier, good immobilization effect and usability are achieved. This method also provides a new class of enzyme immobilization carriers to the current library.

12 Claims, No Drawings

Specification includes a Sequence Listing.

(56) References Cited

OTHER PUBLICATIONS

Yujiro Nomura, The Chemistry of Enamines, Journal of Synthetic Organic Chemistry, Japan, 1961, vol. 19, Issue 11, pp. 801-808, Released on J-Stage Oct. 20, 2010, Online ISSN 1883-6526, Print ISSN 0037-9980, https://doi.org/10.5059/yukigoseikyokaishi.19.801, https://www.jstage.jst.go.jp/article/yukigoseikyokaishi1943/19/11/19_11_801/_article/-char/en, with English abstract (9 pages).
International Search Report, with a mailing date of Dec. 30, 2021, in International application No. PCT/CN2021/092799, filed on May 10, 2021.

* cited by examiner

AMINATION METHOD FOR POLYSTYRENE-TYPE RESIN, AND METHOD FOR IMMOBILIZING ENZYME USING AMINATED RESIN

CROSS-REFERENCE TO RELATED APPLICATION

The present application is a National Stage of International Patent Application No. PCT/CN2021/092799, filed on May 10, 2021, and claims the priority of Chinese Patent Application 202110329787.6 filed on Mar. 29, 2021, the disclosures of which are incorporated by reference in their entirety.

SEQUENCE LISTING

The instant application contains a Sequence Listing which has submitted electronically in ASCII format and is hereby incorporated by reference in its entirety. Said ASCII copy is named PN214449 SEQ_LIST.txt and is 4,320 bytes in size. The sequence listing contains one sequence, which is identical in substance to the sequences disclosed in the PCT application, except that the priority has been added, so no new matter is added.

TECHNICAL FIELD

The present disclosure relates to the technical field of enzyme immobilization, in particular to an amination method for a polystyrene-type resin, and a method for immobilizing an enzyme using an aminated polystyrene-type resin.

BACKGROUND

Compared with chemical catalysts, biocatalysts (enzymes) are widely used in industrial production processes due to their high activity, selectivity and substrate specificity. Biocatalysis is therefore becoming an important part in manufacturing plans for chemical drugs, intermediates, fine chemicals and final drug molecules. Although the enzyme has the high regioselectivity, high catalytic efficiency and mild reaction conditions, free enzymes often suffer from inactivation problems due to fluctuations in temperature, pH, solvent environment and other factors. As process requirements continue to expand, so do the demands on the efficiency and economy of enzyme applications. Therefore, this requires not only enhanced enzyme activity, specificity, and productivity, but also improved enzyme recyclability and reusability.

A good solution to the aforementioned problem is to utilize heterogeneous catalyst systems by enzyme immobilization. The unique catalytic performances of the enzymes are retained, while new advantages such as high stability, easy separation and recovery, superior resuability, and process simplification can be introduced as well. The performance of the immobilized enzyme mainly depends on immobilization methods and carrier materials used. According to different binding modes between the enzyme and the carrier, common methods used for enzyme immobilization may include adsorption, covalent binding, cross-linking and encapsulation and the like. Herein the adsorption method is a combination of physical adsorption, Van der Waals force and hydrophobic effect and the like between the enzyme and the carrier, and is the most commonly used method for the immobilized enzyme because of the advantages of simple and convenient operation, large adsorption capacity and low cost in industrial applications. However, due to the weak binding force between the carrier and the enzyme by the physical adsorption, there is a problem that the enzyme is fallen off from the carrier during repeated use, so that the conversion rate is decreased. Covalent binding, on the other hand, is to link the enzyme and the carrier by a covalent bond. Therefore, the carrier must have a corresponding functional group that may react with the enzyme to generate the covalent bond. Compared with the adsorption method, the linkage between the enzyme and the carrier is stronger, and the problem that the enzyme is fallen off in the use process is solved, thus the stability and cyclicity are better.

In the early 1970s, Davankov et. al. prepared a type of a porous polymer with unique structure and excellent performance by crosslinking of linear polystyrene or re-crosslinking of loosely crosslinked polystyrene by Friedel-Crafts reaction. This type of the reactions is known as ultra-high crosslinking reaction (or Davankov ultra-high crosslinking reaction). The porous polymer prepared by such reaction is called ultra-high crosslinked adsorption resin. Ultra-high crosslinked adsorption resin is considered as the third-generation adsorption resin, in comparison of gel-type and macroporous-type adsorption resins. The ultra-high crosslinking adsorption resin typically has the structural characteristics such as large specific surface area, small average pore size, narrow pore size distribution, and good mechanical strength. At present, it shows broad application prospects in treatment of toxic organic wastewater, extraction of traditional Chinese herbs and antibiotics, gas storage and separation, as well as several other fields.

Due to the ideal reactivity of amino groups, strong electron acceptability and easy protonation, aminated polystyrene resins have seen wide applications in the fields of separation and purification of organic drugs, biomedical polymer materials, adsorption of contaminants in sewage treatment, polymeric catalyst supports and the like. The following methods can be used for synthesizing aminated polystyrene resin:

Nitro compound reduction method: it is an important method to synthesize the aminated polystyrene resin by reducing a nitro compound to obtain an amino compound. There are many process routes, mainly including the following modes:

Catalytic hydrogenation reduction: the catalytic hydrogenation reduction method mainly uses noble metals or alloys thereof as catalysts, such as Ni, Pd, and Pt. While the reaction conditions reach a certain temperature and pressure, the nitro group is reduced to the amino group. The method has many advantages, firstly, it may reduce the manpower investment and has the strong mechanical operability; and secondly, the yield is higher, the product purity is high, the reaction steps are controllable, and it is green and pollution-free. However, it requires noble metal catalysis during the process, and requires the high temperature and pressure, the requirements for devices are higher. These undoubtedly greatly increase the cost of material synthesis.

Hydrazine hydrate reduction method: in the method, the catalysts need to be added to promote the reaction. One commonly used catalyst is the noble metals and the alloys thereof, usually including Pd/C, Pt/C, Raney Ni and the like.

Metal reduction method: the method is applied earlier, specifically by coexisting metals with acids, and also by dissolving salt electrolytes in water to achieve the reduction reaction of the nitro group. It is known by theoretical analysis that metals with electromotive forces before H, such as Li, Na, K, and Mg, may all be used as reducing agents under certain conditions. However, the drawback is that iron sludge is generated at the end of the reaction, and it may cause serious pollution to the environment.

Bromination-amination method: A p-bromine atom is firstly introduced onto phenyl ring by electrophilic substitution reaction. The obtained resin is then reacted with LIN$(SiMe_3)_2$ with the existence of a palladium catalyst. Finally, p-aminopolystyrene resin is afforded with post-treatment using acid or alkali.

Chloromethylated polystyrene amination method: Firstly, polystyrene microspheres are linked to a chloromethyl in the para-position of the benzene ring by a chloromethylation reaction, and are then subjected to an amination reaction with an amination reagent to prepare aminopolystyrene. However, the method requires chloromethyl methyl ether or dichloromethyl methyl ether, these chemical reagents are harmful to human bodies and have a strong cancer risk, and are therefore widely banned for use internationally. In addition, the reaction is also accompanied by side reactions such as multi-substitution and post-crosslinking, so that the chloromethyl resin structure becomes complex.

Chloroacetylated polystyrene amination method: an acyl group is introduced into the para-position of the benzene ring by an Friedel-Crafts acylation reaction, and then aminated polystyrene is prepared by the amination reaction, as follows:

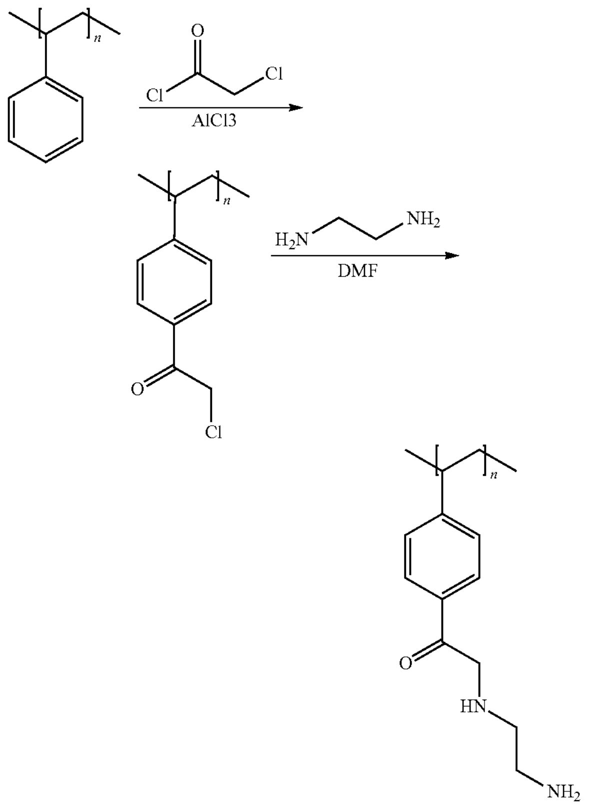

SUMMARY

A main purpose of the present disclosure is to provide a new amination method for a polystyrene-type resin, and to use an aminated polystyrene-type resin as an enzyme immobilization carrier to immobilize a transaminase. The method not only provides a new method for synthesis of the aminated polystyrene resin, but also provides a new class of enzyme immobilization carriers to the current library.

In order to achieve the above purpose, according to one aspect of the present disclosure, an amination method for a polystyrene-type resin is provided, and the amination method includes: in a solvent, a catalyst is used to catalyze a polystyrene-type resin and an enamine salt to perform a Friedel-Crafts alkylation reaction, to obtain an aminated polystyrene-type resin, herein the catalyst is a Lewis acid catalyst.

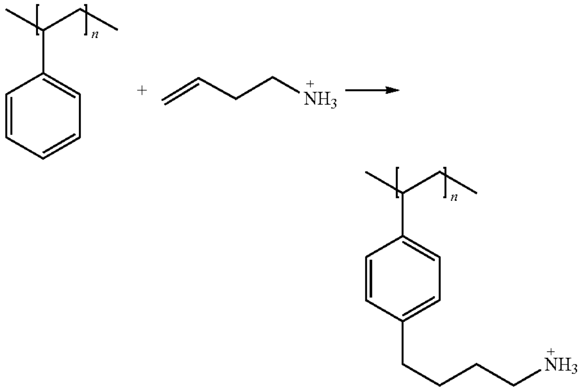

Furthermore, the temperature of the above Friedel-Crafts alkylation reaction is 40~80° C., and preferably, the time of the Friedel-Crafts alkylation reaction is 12~20 h.

Further, the mass ratio of the above polystyrene-type resin to the enamine salt is 2:1~2:3.

Further, the molar ratio of the above enamine salt to the Lewis acid catalyst is 1:3~1:5.

Further, the above Lewis acid catalyst is selected from anhydrous aluminum trichloride or ferric trichloride.

Further, the above enamine salt is 3-butenamine hydrochloride.

Further, the above solvent is 1,2-dichloroethane.

Further, the above polystyrene-type resin is selected from any one of polystyrene resin, polystyrene-methacrylate resin, AB8 polystyrene resin, ECR1090 polystyrene resin, NKA9 polystyrene resin, D101 polystyrene resin, and SXD11 polystyrene resin.

Further, the above amination method includes: the polystyrene-type resin and enamine salt are dispersed in the solvent to form a system to be reacted; and in a nitrogen or inert atmosphere, the system to be reacted is mixed with the catalyst and heated to the temperature of the Friedel-Crafts alkylation reaction to perform the Friedel-Crafts alkylation reaction, to obtain the aminated polystyrene-type resin.

According to another aspect of the present disclosure, a method for immobilizing an enzyme using an aminated polystyrene-type resin is provided, and the method includes: the aminated polystyrene-type resin is prepared by using any one of the above amination methods; and the aminated polystyrene-type resin is used as a carrier, to immobilize the enzyme by using glutaraldehyde as a crosslinking agent.

Further, the above method includes: the aminated polystyrene-type resin is modified with a buffer solution of the glutaraldehyde, to obtain a glutaraldehyde-modified resin; and enzyme solution is crosslinked with the glutaraldehyde-modified resin, to achieve immobilization.

Further, the above method includes: the enzyme solution is mixed with the aminated polystyrene-type resin, to obtain a resin adsorbed with the enzyme; and the resin adsorbed with the enzyme is crosslinked with the buffer solution of the glutaraldehyde, to achieve immobilization.

Further, the above buffer solution of the glutaraldehyde includes a phosphate buffer solution, the mass content of the glutaraldehyde in the buffer solution of the glutaraldehyde is 1~2%, and the enzyme is a transaminase.

By applying technical schemes of the present disclosure, the present application utilizes the Friedel-Crafts alkylation reaction to graft the enamine salt onto the polystyrene-type resin in one step, and the amination of the polystyrene-type resin is completed. The conditions of the Friedel-Crafts alkylation reaction are easy to control, the post-treatment process is simple, and it is only necessary to remove the catalyst and the unreacted enamine salt by washing, such that the above amination method in the present application has few steps and is simple and easy to implement. Meanwhile, the amination method further avoids the use of a noble metal catalyst, thereby reducing the production cost. The commercial polystyrene resin modified by amination may be successfully used as an enzyme immobilization carrier, and has better immobilization effects and reusability. The present application also provides new insights for the design of enzyme immobilization carrier, so that more selections for immobilization of the different enzymes are provided in terms of carrier pore size, specific surface area, skeleton structure, carrier polarity, and other aspects.

DETAILED DESCRIPTION OF THE EMBODIMENTS

It should be noted that examples and features in the present application may be combined with each other if no other conflicts exist. The present disclosure is described in detail below in combination with examples.

As analyzed in the background of the present application, the preparation method for the aminated polystyrene-type resin in prior art may use a complex preparation method, require a plurality of steps or multiple post-treatment methods. In order to address the problem, the present application provides a facile amination method for a polystyrene-type resin, and a method for immobilizing an enzyme using an aminated polystyrene-type resin.

In a typical embodiment of the present application, an amination method for a polystyrene-type resin is provided, and the amination method includes: in a solvent, a catalyst is used to catalyze a polystyrene-type resin and an enamine salt to perform a Friedel-Crafts alkylation reaction, to obtain an aminated polystyrene-type resin, herein the catalyst is a Lewis acid catalyst.

The present application achieves amination of polystyrene-type resin by utilizing the Friedel-Crafts alkylation reaction to graft the enamine salt onto the polystyrene-type resin. The conditions of the Friedel-Crafts alkylation reaction are easy to control, the post-treatment process is simple, and it is only necessary to remove the catalyst and the unreacted enamine salt by washing. Therefore, the above amination method in the present application has fewer steps and is simple and easy to implement. Meanwhile, the amination method further avoids the use of a noble metal catalyst, thereby the production cost is reduced. The commercial polystyrene resins modified by aforementioned amination method may be successfully used as an enzyme immobilization carriers, and exhibit good immobilization effects and reusability. The present application also provides new insights for the design of enzyme immobilization carrier, so that more selections for immobilization of the different enzymes are provided in terms of carrier pore size, specific surface area, skeleton structure, carrier polarity, and other aspects.

In order to improve the efficiency of the above Friedel-Crafts alkylation reaction, for the above reaction raw materials, preferably the temperature of the above Friedel-Crafts alkylation reaction is 40~80° C., and preferably the time of the Friedel-Crafts alkylation reaction is 12~20 h.

The above Friedel-Crafts alkylation reaction essentially involves grafting an alkyl group with an amino group onto a benzene ring of polystyrene. Due to the macromolecular characteristics of the polystyrene-type resin, it is difficult to achieve uniform grafting on each benzene ring. In order to improve the amount of amino groups grafted onto polystyrene-type resins, preferably the molar ratio of the above polystyrene-type resin to the enamine salt is 2:1~2:3.

In addition, in order to improve catalytic efficiency, avoid catalyst waste, and facilitate catalyst removal, preferably the molar ratio of the above enamine salt to the Lewis acid catalyst is 1:3~1:5.

In the above method, the Lewis acid catalyst used for the Friedel-Crafts alkylation reaction may be selected from Lewis acid catalysts commonly used for the Friedel-Crafts alkylation reaction in prior art. In order to facilitate catalyst removal and ensure efficient catalysis, preferably the above Lewis acid catalyst is any one of anhydrous aluminum trichloride and ferric trichloride or a combination thereof.

In some embodiments, the enamine salt used for the above amination method is 3-butenamine hydrochloride, to achieve efficient amination.

The above solvent used in the present application is mainly for dissolving the enamine salt and Lewis acid catalyst, in order to facilitate its full contact with the polystyrene-type resin. In order to improve the solubility of the enamine salt and Lewis acid catalyst, preferably the above solvent is 1,2-dichloroethane.

The polystyrene-type resin used in the present application includes but not limited to any one of polystyrene resin, polystyrene methacrylate resin, AB8 polystyrene resin, ECR1090 polystyrene resin, NKA9 polystyrene resin, D101 polystyrene resin, and SXD11 polystyrene resin. Whether it is a pure polystyrene resin or a modified polystyrene resin, the above amination method may be used for amino modification.

In some embodiments of the present application, the above amination method includes: the polystyrene-type resin and the enamine salt are dispersed in the solvent, to form a system to be reacted; and in a nitrogen or inert atmosphere, the system to be reacted is mixed with the catalyst and heated to the temperature of the Friedel-Crafts alkylation reaction to perform the Friedel-Crafts alkylation reaction, obtaining the aminated polystyrene-type resin. The enamine salt and the polystyrene-type resin are dispersed in the solvent, so that the enamine salt may enter the pores of the polystyrene-type resin in advance, then the catalyst is added for the Friedel-Crafts alkylation reaction, ensuring faster reaction and a uniform alkylation.

In another typical embodiment of the present application, a method for immobilizing an enzyme using an aminated polystyrene-type resin is provided, and the method includes: the aminated polystyrene-type resin is prepared by any one of the above amination methods; and the aminated polystyrene-type resin is used as a carrier, to immobilize the enzyme by using glutaraldehyde as a crosslinking agent.

The aforementioned preparation method for aminoated polystyrene-type resins benefits from merits such as facile operation and low production cost. The degree of amination can be flexibly adjusted in this aminoation method, thereby controlling the degree of enzyme immobilization in the next steps.

In some embodiments of the present application, the above method includes: the aminated polystyrene-type resin is modified with a buffered solution of glutaraldehyde, to obtain a glutaraldehyde-modified resin; and enzyme solution is crosslinked with the glutaraldehyde-modified resin to achieve immobilization.

In the above method firstly uses the glutaraldehyde to modify the resin, as to use the amino group on the polystyrene-type resin to crosslink with the glutaraldehyde to form a crosslinking network; and then, amine groups on the enzyme is crosslinked with the glutaraldehyde to achieve crosslinking and curing of the enzyme. This procedure makes the crosslinking and curing efficiency of the enzyme higher, especially for enzymes that are sensitive to the glutaraldehyde.

In other embodiments of the present application, the above method includes: the enzyme solution is mixed with the aminated polystyrene-type resin, to obtain a resin adsorbed with the enzyme; and the resin adsorbed with the enzyme is crosslinked with a buffered solution of glutaraldehyde, to achieve immobilization.

In the above method, the enzymes are firstly adsorbed onto the internal and external surfaces of the polystyrene-type resin by the adsorption action, and then reacts with the glutaraldehyde, to achieve the use of the glutaraldehyde to immobilize the enzyme on the polystyrene-type resin by a crosslinking mode. The above method is particularly applicable to enzymes that are not sensitive to the glutaraldehyde.

The buffered solution for glutaraldehyde used in the present application may be a conventional buffer solution used for crosslinking and curing. For example, the above buffer solution of the glutaraldehyde includes the phosphate buffer solution. In addition, in order to improve the immobilization rate of enzyme, preferably the mass content of the glutaraldehyde in the above buffered solution of the glutaraldehyde is 1~2%, as to improve the utilization rate of the glutaraldehyde. In the process of immobilizing the enzyme, the loading amount may be adjusted by varying the ratio of enzyme to the carrier, which is already well known in the art.

Since the above immobilization uses the crosslinking action between the aldehyde group of the glutaraldehyde and the amino group on the enzyme, the method of the present application is applicable to conventional enzymes, for example, the above enzyme is selected from a transaminase.

The beneficial effects of the present application are further described below in combination with embodiments and contrast examples.

EXAMPLES OF AMINATION

Example 1-1

Synthesis of Polystyrene Resin 150 mL of aqueous solution containing 0.5% polyvinyl alcohol (PVA) was added to a 500 mL four-necked flask, and the temperature was increased to 40° C. 16 g of styrene, 5 g of divinylbenzene (80%), 10 mL of toluene, 20 mL of n-heptane, and 100 mg of benzoyl peroxide were mixed evenly, and then added into the four-necked flask. The droplet size were adjusted to an appropriate range by controlling stirring speed, and the temperature was increased to 80° C. and kept for 2 h, and then 88° C. and kept for 4 h. After the reaction was completed, it was cooled to room temperature. The obtained polystyrene resins were washed sequentially with hot water, ethanol, and deionized water, and finally screened and dried.

Amination of Polystyrene Resin 1 g of a dried polystyrene resin and 1 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated polystyrene resin: PS—$NH_2$.

Example 1-2

Synthesis of Polystyrene-Methacrylate Resin 240 mL of aqueous solution containing 0.5% PVA and 10% NaCl was added to a 500 mL four-necked flask, and the temperature was increased to 40° C. 6 g of methyl methacrylate, 15 g of divinylbenzene (80%), 20 mL of 1,2-dichloroethane, 40 mL of methylcyclohexane and 100 mg of azobisisobutyronitrile were mixed evenly, and then added into the four-necked flask. The droplet size were adjusted to an appropriate range by controlling stirring speed, and the temperature was increased to 70° C. and kept for 2 h, and then 80° C. and kept for 4 h, and finally 85° C. for 1 h. After the reaction was completed, it was cooled to a room temperature. The obtained PDMA resins were washed sequentially with hot water, ethanol, and deionized water, and finally screened and dried.

PDMA Resin Modification 1 g of a dried PDMA resin and 0.7 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated polystyrene resin: PDMA-$NH_2$.

Example 1-3

1 g of a dried ECR1090 polystyrene resin (purchased from Purolite) and 1 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated polystyrene resin: ECR1090-$NH_2$.

Example 1-4

1 g of a dried AB8 resin (purchased from Tianjin Nankai Hecheng Science & Technology Co., Ltd.) and 1 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated AB8 resin: AB8-$NH_2$.

Example 1-5

1 g of a dried NKA9 resin (purchased from Tianjin Nankai Hecheng Science & Technology Co., Ltd.) and 1 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated NKA9 resin: NKA9-$NH_2$.

Example 1-6

40. 1 g of a dried SXD-11 resin (purchased from Anhui Sanxing Co., Ltd.) and 1 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated SXD-11 resin: SXD-11-$NH_2$.

Example 1-7

1 g of a dried D101 resin (purchased from Anhui Sanxing Co., Ltd.) and 1 g of 3-butenamine hydrochloride were dispersed into 100 mL of 1,2-dichloroethane and stirred at room temperature for 1 h. Then 2 g of anhydrous aluminum trichloride was weighed and added to the above mixture and the stirring was allowed to continue for another 10 min. Then the temperature was increased to 80° C. and the reaction was allowed to go on for another 20 h under the protection of $N_2$. After the reaction was completed, it was cooled to room temperature and washed sequentially with methanol and deionized water to obtain an aminated D101 resin: D101-$NH_2$.

The amino contents of the aminated polystyrene resins obtained from the above examples are detected by ninhydrin color development method and acid-base titration method, their specific surface areas and pore sizes are measured by nitrogen adsorption-desorption method. The results are shown in Table 1.

TABLE 1

| Name | Specific surface area ($m^2$ $g^{-1}$) | Average pore size (nm) | Amino content (mmol/g) |
|---|---|---|---|
| PS-$NH_2$ | 750 | 2.3 | 5.2 |
| PDMA-$NH_2$ | 420 | 10 | 2.1 |
| AB8-$NH_2$ | 520 | 8 | 3.8 |
| ECR1090-$NH_2$ | 610 | 50 | 2.8 |
| NKA9-$NH_2$ | 150 | 10 | 3.2 |
| D101-$NH_2$ | 450 | 5 | 3.8 |
| SXD11-$NH_2$ | 400 | 20 | 2.5 |

Examples of Enzyme Immobilization

A transaminase is used as a model, and a transaminase derived from *Chromobacterium violaceum* DSM30191 (CVTA) is used as a model substance, and its sequence SEQ ID NO. 1 is:

```
MQKQRTCSQWRELDAAHHLHPFTDTASLNQAGARVMTRGEGVYLWD
CEGNKIIDGMAGLWCVNVGYGRKDFAEAARRQMEELPFYNTFFGT
THPPVVELSSLLAEVTPAGFDRVFYTNSGSESVDTMIRMVRRYWD
VQGKPEKKTLIGRWNGYHGSTIGGASLGGMKYMHEQGDLPIPGMA
HIEQPWWYKHGKDMTPDEFGVVAARWLEEKILEIGADKVAAFVGE
PIQGAGGVIVPPATYWPEIERICRKYDVLLVADEVICGFGRTGEW
FGHQHFGFQPDLFTAAKGLSSGYLPLGAVFVGDRVAEGLIAGGDF
NHGFTYSGHPVCAAVAHANVAALRDEGIVQRVKDDIGPYMQKRWR
ETFSRFEHVDDVRGVGMMLAFTLVKNKAKRELFPDFGEIGTLCED
IFFRNNLIMTAQGDHIVSAPPLVMTRAEVDEMLAVAERCLEEFEQ
TLKARGLA.
```

Example 2-1

1% glutaraldehyde solution was prepared with 20 mM phosphate buffer solution (pH=7.0). 1 g of the aminated polystyrene resin and a pristine polystyrene resin in Example 1-1 were weighed respectively and dispersed into the above solution. It was incubated at 30° C. for 1 h, and then washed three times with deionized water, to obtain a red glutaraldehyde-modified aminated polystyrene resin and a glutaraldehyde-modified pristine polystyrene resin. The resin might become red brown after being modified with the glutaraldehyde, so it was judged whether the glutaraldehyde is successfully modified according to the color change.

1 g of glutaraldehyde-modified aminated polystyrene resin and glutaraldehyde-modified pristine polystyrene resin were added to an enzyme solution (4 mL, 1 V enzyme solution plus 3 V phosphate buffer solution) to prepare an aminated polystyrene immobilized enzyme and a pristine polystyrene resin immobilized enzyme.

The enzyme loading amount was calculated by measuring the difference of the protein concentration before and after immobilization. The loading of enzyme on the aminated polystyrene immobilized enzyme was 26.44 mg/g; and the loading of enzyme on the pristine polystyrene resin immobilized enzyme was 11.09 mg/g.

Example 2-2

1% glutaraldehyde solution was prepared with 20 mM phosphate buffer solution (pH=7.0). 1 g of the PDMA-$NH_2$ resin and PDMA resin in Example 1-2 were weighed respectively and dispersed into the above solution. It was incubated at 30° C. for 1 h, and then washed three times with deionized water, a red glutaraldehyde-modified PDMA resin and a glutaraldehyde-modified PDMA-$NH_2$ resin.

1 g of glutaraldehyde-modified PDMA resin and glutaraldehyde-modified PDMA-$NH_2$ resin were added to an enzyme solution (4 mL, 1 V enzyme solution plus 3 V phosphate buffer solution) to prepare PDMA-$NH_2$ and PDMA immobilized enzymes, respectively.

The enzyme loading amount was calculated by measuring the difference of the protein concentration before and after immobilization. The loading of enzyme on the PDMA-NH2 immobilized enzyme was 28.35 mg/g; and the loading of enzyme on the PDMA immobilized enzymes was 9.17 mg/g.

Example 2-3

1% glutaraldehyde solution was prepared with 20 mM phosphate buffer solution (pH=7.0). 1 g of the ECR1090-$NH_2$ resin and ECR1090 resin in Example 1-3 were weighed respectively and dispersed into the above solution. It was incubated at 30° C. for 1 h, and then washed three times with deionized water, to obtain a red glutaraldehyde-modified ECR1090 resin and a glutaraldehyde-modified ECR1090-$NH_2$ resin.

1 g of glutaraldehyde-modified ECR1090-$NH_2$ resin and glutaraldehyde-modified ECR1090 resin were added to an enzyme solution (4 mL, 1 V enzyme solution plus 3 V phosphate buffer solution) to prepare ECR1090-$NH_2$ and ECR1090 immobilized enzymes, respectively.

The enzyme loading amount was calculated by measuring the difference of the protein concentration before and after immobilization. The loading of enzyme on the ECR1090-NH2 immobilized enzyme was 21.82 mg/g; and the loading of enzyme on the ECR1090 immobilized enzyme was 21.09 mg/g.

Example 2-4

1% glutaraldehyde solution was prepared with 20 mM phosphate buffer solution (pH=7.0). 1 g of the AB8-$NH_2$ resin and AB8 resin in Example 1-4 were weighed respectively and dispersed into the above solution. It was incubated at 30° C. for 1 h, and then washed three times with deionized water, to obtain a red glutaraldehyde-modified AB8 resin and a glutaraldehyde-modified AB8-$NH_2$ resin.

1 g of glutaraldehyde-modified AB8-$NH_2$ resin and glutaraldehyde-modified AB8 resin were added to an enzyme solution (4 mL, 1 V enzyme solution plus 3 V phosphate buffer solution) to prepare AB8-$NH_2$ and AB8 immobilized enzymes, respectively.

The enzyme loading amount was calculated by measuring the difference of the protein concentration before and after immobilization. The loading of enzyme on the AB8-NH2 immobilized enzyme was 28.37 mg/g; and the loading of enzyme on the AB8 immobilized enzyme was 12.91 mg/g.

Example 2-5

1% glutaraldehyde solution was prepared with 20 mM phosphate buffer solution (pH=7.0). 1 g of the NKA9-$NH_2$ resin and NKA9 resin in Example 1-5 were weighed respectively and dispersed into the above solution. It was incubated at 30° C. for 1 h, and then washed three times with deionized water, to obtain a red glutaraldehyde-modified NKA9 resin and a glutaraldehyde-modified NKA9-$NH_2$ resin.

1 g of glutaraldehyde-modified NKA9-$NH_2$ resin and glutaraldehyde-modified NKA9 resin were added to an enzyme solution (4 mL, 1 V enzyme solution plus 3 V phosphate buffer solution) to prepare NKA9-$NH_2$ and NKA9 immobilized enzymes, respectively.

The enzyme loading amount was calculated by measuring the difference of the protein concentration before and after immobilization. The loading of enzyme on the NKA9-NH2 immobilized enzyme was 44.56 mg/g; and the loading of enzyme on the NKA9 immobilized enzyme was 42.31 mg/g.

Example 2-6

1% glutaraldehyde solution was prepared with 20 mM phosphate buffer solution (pH=7.0). 1 g of the SXD-11-$NH_2$ resin and SXD-11 resin in Example 1-5 were weighed respectively and dispersed into the above solution. It was incubated at 30° C. for 1 h, and then washed three times with deionized water, to obtain a red glutaraldehyde-modified SXD-11 resin and a glutaraldehyde-modified SXD-11-$NH_2$ resin.

1 g of glutaraldehyde-modified SXD-11-$NH_2$ resin and glutaraldehyde-modified SXD-11 resin were added to an enzyme solution (4 mL, 1 V enzyme solution plus 3 V phosphate buffer solution) to prepare SXD-11-$NH_2$ and SXD-11 immobilized enzymes, respectively.

The enzyme loading amount was calculated by measuring the difference of the protein concentration before and after immobilization. The loading of enzyme on the SXD-11-NH2 immobilized enzyme was 13.31 mg/g; and the loading of enzyme on the SXD-11 immobilized enzyme was 13.41 mg/g.

The following enzymatic reaction was employed:

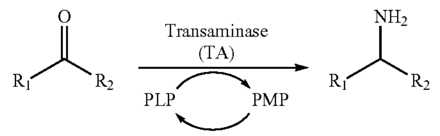

In a 20 mL reaction flask, 0.5 mL of methanol was added to dissolve 0.1 g of a carbonyl substrate, and 15 eq of isopropylamine hydrochloride and 25.0 mg of 5'-pyridoxal phosphate (PLP) were added, 0.1 M phosphate buffer solution (pH 8.0) was added until the final volume of reaction solution reached 5 mL, to form a system to be reacted; and 0.1 g of transaminase powder or 0.1 g of an immobilized enzyme (prepared with the transaminase powder) was respectively added to the system to be reacted independently, and the mixture was stirred at 47° C. for 20 h. The conversion rate of the system was detected by high performance liquid chromatography (HPLC). After each round of the reaction, the immobilized enzymes were separated and used in the next round of the reaction to test their reusability. The results were shown in Table 2.

TABLE 2

| Enzyme | Example | Carrier | Conversion rate (%) | Cycle count |
|---|---|---|---|---|
| Transaminase | | Free enzyme | 99 | 1 |
| derived from | Example 2-1 | PS | 9 | 1 |
| *Chromobacterium* | | PS-$NH_2$ | 87 | 10 |
| *violaceum* | Example 2-2 | PDMA | 13 | 1 |
| DSM30191 | | PDMA-$NH_2$ | 90 | 10 |

TABLE 2-continued

| Enzyme | Example | Carrier | Conversion rate (%) | Cycle count |
|---|---|---|---|---|
| | Example 2-3 | ECR1090 | 20 | 1 |
| | | $ECR1090-NH_2$ | 98 | 10 |
| | Example 2-4 | AB8 | 1 | 1 |
| | | $AB8-NH_2$ | 80 | 10 |
| | Example 2-5 | NK9 | 36 | 1 |
| | | $NK9-NH_2$ | 95 | 10 |
| | Example 2-6 | SXD-11 | 3 | 1 |
| | | $SXD-11-NH_2$ | 95 | 10 |

From the above description, it can be seen that the above examples of the present disclosure achieved the following technical effects.

The present application utilizes the Friedel-Crafts alkylation reaction to graft the enamine salt onto the polystyrene-type resin, and the amination of the polystyrene-type resin is completed. The conditions of the Friedel-Crafts alkylation reaction are easy to control, the post-treatment process is simple, and it is only necessary to remove the catalyst and the unreacted enamine salt by washing. Therefore, the above amination method in the present application has few steps and is simple and easy to implement. Meanwhile, the amination method further avoids the use of a noble metal catalyst, thereby the production cost is reduced. The commercial polystyrene resins modified by aforementioned amination method may be successfully used as an enzyme immobilization carrier, and exhibit good immobilization effects and reusability. The present application also provides new insights for the design of enzyme immobilization carrier, so that more selections for immobilization of the different enzymes are provided in terms of carrier pore size, specific surface area, skeleton structure, carrier polarity, and other aspects.

It should be understood that the examples described above are only intended to illustrate, but not limit the scope of the invention. Those skilled in the art will recognize many equivalents and modifications to the specific embodiments described herein. These equivalents and modifications are intended to be encompassed in the following claims appended hereto as permitted by applicable law.

What is claimed is:

1. An amination method for a polystyrene resin, said amination method comprising:

reacting polystyrene resin and an enamine salt by Friedel-Crafts alkylation reaction in a solvent, in the presence of a Lewis acid catalyst; wherein the enamine salt is 3-butenylamine hydrochloride.

2. The amination method according to claim 1, wherein a temperature of the Friedel-Crafts alkylation reaction is 40-80° C., and a time of the Friedel-Crafts alkylation reaction is 12-20 h.

3. The amination method according to claim 1, wherein a mass ratio of the polystyrene resin and the enamine salt is 2:1 to 2:3.

4. The amination method according to claim 1, wherein a molar ratio of the enamine salt and the Lewis acid catalyst is 1:3 to 1:5.

5. The amination method according to claim 1, wherein the Lewis acid catalyst is anhydrous aluminum trichloride, iron trichloride or a combination thereof.

6. The amination method according to claim 1, wherein the solvent is 1,2-dichloroethane.

7. The amination method according to claim 1, comprising:

dispersing the polystyrene resin and the enamine salt in the solvent to form a system to be reacted;

mixing the system to be reacted with the catalyst, heating to a temperature of Friedel-Crafts alkylation reaction under inert atmosphere, and performing the Friedel-Crafts alkylation reaction, to obtain the aminated polystyrene resin.

8. A method for immobilizing an enzyme with an aminated polystyrene resin, wherein the method comprises:

preparing the aminated polystyrene resin by the amination method according to claim 1; and immobilizing the enzyme with the aminated polystyrene resin as a carrier, and glutaraldehyde as a cross-linking agent.

9. The method according to claim 8, wherein the method comprises:

modifying the aminated polystyrene resin by a buffer solution of the glutaraldehyde, to obtain a glutaraldehyde-modified resin; and performing a cross-linking reaction on an enzyme solution and the glutaraldehyde-modified resin, to achieve the immobilization.

10. The method according to claim 8, wherein the method comprises:

mixing the enzyme solution with the aminated polystyrene resin, to obtain an enzyme-adsorbed resin; and performing a cross-linking reaction on the enzyme-adsorbed resin and a buffer solution of the glutaraldehyde, to achieve the immobilization.

11. The method according to claim 9, wherein the buffer solution of the glutaraldehyde comprises a phosphate buffer solution, a mass content of the glutaraldehyde in the buffer solution of the glutaraldehyde is 1-2%, and the enzyme is a transaminase.

12. The method according to claim 10, wherein the buffer solution of the glutaraldehyde comprises a phosphate buffer solution, a mass content of the glutaraldehyde in the buffer solution of the glutaraldehyde is 1-2%, and the enzyme is a transaminase.

* * * * *

SEQUENCE LISTING

```
<160> NUMBER OF SEQ ID NOS: 1

<210> SEQ ID NO 1
<211> LENGTH: 459
<212> TYPE: PRT
<213> ORGANISM: Chromobacterium violaceum DSM30191

<400> SEQUENCE: 1

Met Gln Lys Gln Arg Thr Cys Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Cys Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Gly Thr Thr His Pro Pro Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
    130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220
```

-continued

```
Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Leu Gly Ala Val Phe Val Gly Asp
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Met Leu Ala Phe Thr Leu
    370                 375                 380

Val Lys Asn Lys Ala Lys Arg Glu Leu Phe Pro Asp Phe Gly Glu Ile
385                 390                 395                 400

Gly Thr Leu Cys Glu Asp Ile Phe Phe Arg Asn Asn Leu Ile Met Thr
                405                 410                 415

Ala Gln Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
    450                 455
```